US008868681B2

(12) United States Patent
Xu et al.

(10) Patent No.: US 8,868,681 B2
(45) Date of Patent: Oct. 21, 2014

(54) METHOD, DEVICE, AND SYSTEM FOR REMOTELY ACQUIRING USER PHYSIOLOGICAL DETECTION DATA

(75) Inventors: Zhongqing Xu, Shenzhen (CN); Changcheng Wen, Shenzhen (CN); Bingfu Wang, Shenzhen (CN)

(73) Assignee: Huawei Technologies Co., Ltd., Shenzhen (CN)

(*) Notice: Subject to any disclaimer, the term of this patent is extended or adjusted under 35 U.S.C. 154(b) by 41 days.

(21) Appl. No.: 13/306,474

(22) Filed: Nov. 29, 2011

(65) Prior Publication Data

US 2012/0072536 A1      Mar. 22, 2012

Related U.S. Application Data

(63) Continuation of application No. PCT/CN2010/077173, filed on Sep. 21, 2010.

(30) Foreign Application Priority Data

Oct. 30, 2009   (CN) .......................... 2009 1 0109932

(51) Int. Cl.
| | |
|---|---|
| *G06F 15/16* | (2006.01) |
| *G08B 23/00* | (2006.01) |
| *G06F 19/00* | (2011.01) |
| *A61B 5/00* | (2006.01) |
| *G06F 21/60* | (2013.01) |
| *G06F 21/62* | (2013.01) |

(52) U.S. Cl.
CPC ............ *G06F 19/327* (2013.01); *G06F 21/606* (2013.01); *G06F 19/322* (2013.01); *G06F 19/3418* (2013.01); *A61B 5/0015* (2013.01); *G06F 21/6245* (2013.01)
USPC ......................................... 709/217; 340/573

(58) Field of Classification Search
USPC ......................................... 340/573; 709/217
See application file for complete search history.

(56) References Cited

U.S. PATENT DOCUMENTS

| | | | | |
|---|---|---|---|---|
| 4,958,645 | A | * | 9/1990 | Cadell et al. .................. 600/484 |
| 5,944,659 | A | * | 8/1999 | Flach et al. .................... 600/300 |

(Continued)

FOREIGN PATENT DOCUMENTS

| | | |
|---|---|---|
| CN | 1313697 A | 9/2001 |
| CN | 1377492 A | 10/2002 |

(Continued)

OTHER PUBLICATIONS

European Patent Office Communication related to Application No. 10826031.6-2201, pursuant to Rule 62 EPC, the supplementary European search report (Art. 153(7) EPC) and the European search opinion, dated (mailed) Jun. 18, 2012.

(Continued)

*Primary Examiner* — Emmanuel L Moise
*Assistant Examiner* — Mahran Abu Roumi
(74) *Attorney, Agent, or Firm* — Conley Rose, P.C.; Grant Rodolph; Nicholas K. Beaulieu

(57) ABSTRACT

A method, a device, and a system for remotely acquiring user physiological detection data are provided according to embodiments of the present invention. The method includes: receiving detection related information sent by handheld equipment, in which the detection related information includes user identity (ID) information and equipment positioning information; sending a detection start instruction to corresponding medical detection equipment according to the equipment positioning information; receiving user physiological detection data sent by the medical detection equipment, in which the user physiological detection data is associated with an equipment ID of the medical detection equipment; and binding and sending the user physiological detection data and the associated user ID information according to associative information of the user ID information and the equipment ID of the medical detection equipment.

20 Claims, 8 Drawing Sheets

(56) References Cited

U.S. PATENT DOCUMENTS

| | | | |
|---|---|---|---|
| 6,198,394 B1* | 3/2001 | Jacobsen et al. | 340/573.1 |
| 6,954,148 B2* | 10/2005 | Pulkkinen et al. | 340/572.1 |
| 7,912,737 B2* | 3/2011 | Schoenberg | 705/3 |
| 2001/0005842 A1 | 6/2001 | Le Gendre et al. | |
| 2002/0165733 A1* | 11/2002 | Pulkkinen et al. | 705/2 |
| 2003/0147515 A1 | 8/2003 | Kai et al. | |
| 2003/0227386 A1* | 12/2003 | Pulkkinen et al. | 340/573.1 |
| 2004/0170154 A1* | 9/2004 | Carter et al. | 370/338 |
| 2005/0151640 A1* | 7/2005 | Hastings | 340/539.11 |
| 2005/0234307 A1 | 10/2005 | Heinonen et al. | |
| 2006/0129816 A1 | 6/2006 | Hinton et al. | |
| 2007/0105531 A1 | 5/2007 | Schroeder, Jr. | |
| 2007/0180047 A1 | 8/2007 | Dong | |
| 2008/0162185 A1 | 7/2008 | Klabunde et al. | |
| 2009/0090018 A1* | 4/2009 | Stein | 34/60 |
| 2009/0118595 A1 | 5/2009 | Greiner et al. | |
| 2009/0205042 A1 | 8/2009 | Zhou et al. | |
| 2009/0275805 A1* | 11/2009 | Lane et al. | 600/300 |
| 2010/0016924 A1* | 1/2010 | Doerr | 607/60 |
| 2012/0072536 A1* | 3/2012 | Xu et al. | 709/217 |
| 2012/0116803 A1* | 5/2012 | Reid et al. | 705/2 |

FOREIGN PATENT DOCUMENTS

| | | | |
|---|---|---|---|
| CN | 1547142 | A | 11/2004 |
| CN | 1964666 | A | 5/2007 |
| CN | 1968645 | A | 5/2007 |
| CN | 101179985 | A | 5/2008 |
| CN | 101326527 | A | 12/2008 |
| CN | 101385637 | A | 3/2009 |
| CN | 101495030 | A | 7/2009 |
| CN | 101557549 | A | 10/2009 |
| JP | 2007144141 | A | 6/2007 |
| WO | WO 2008/087571 | A2 | 7/2008 |
| WO | 2009124463 | A1 | 10/2009 |
| WO | WO 2011/050668 | | 5/2011 |

OTHER PUBLICATIONS

XP-002498048; Official Journal EPO; Notice from the European Patent Office dated Oct. 1, 2007 concerning business method; pp. 592-593; dated Nov. 2007.

XP002456252; Statement in accordance with the Notice from the European Patent Office dated Oct. 1, 2007 concerning business methods (OJ EPO Nov. 2007, 592-593).

Communication from a foreign counterpart application, International Application No. PCT/CN2010/077173, English Translation, Written Opinion dated Dec. 30, 2010, 4 pages.

International Search Report for International Application No. PCT/CN2010/077173, mailed Nov. 26, 2010 Huawei Technologies C., Ltd 5 pgs.

* cited by examiner

METHOD, DEVICE, AND SYSTEM FOR REMOTELY ACQUIRING USER PHYSIOLOGICAL DETECTION DATA

CROSS-REFERENCE TO RELATED APPLICATIONS

This application is a continuation of International Application No. PCT/CN2010/077173, filed on Sep. 21, 2010, which claims priority to Chinese Patent Application No. 200910109932.9, filed on Oct. 30, 2009, both of which are hereby incorporated by reference in their entireties.

FIELD OF THE INVENTION

The present invention relates to the field of telemedicine technologies, and in particular, to a method, a device, and a system for remotely acquiring user physiological detection data.

BACKGROUND OF THE INVENTION

Telemedicine is a whole new medical service, in which the computer technologies, the communications technologies, and the multimedia technologies are combined with the medical technologies to improve the level of diagnosis and medical treatment, reduce medical expenses, and meet health care demands of the people. Compared with the conventional hospital-based treatment, the telemedicine has the advantages of low cost and convenience to use. In addition, the telemedicine can save the time of patients and doctors, and make full use of the medical resources. Most importantly, with the development of the telemedicine, personal health care and disease prevention can develop rapidly.

The telemedicine technologies mainly include two parts, one is remote diagnostic/therapeutic equipment with communication functions, and the other is a telemedicine network.

FIG. 1 is a schematic structure diagram of a telemedicine health care system in the prior art. In the system, a user medical terminal connected to a detection instrument is connected to central medical website equipment through a network, and is then connected, through the central medical website equipment, to a doctor diagnostic terminal, a medicine/instrument supply terminal, a distribution organization terminal, and a billing server network that is respectively connected to a bank computer terminal and an insurance company computer terminal. The system provides effective means for long-term and real-time monitoring, diagnosis, and treatment of patients of various diseases, and provides services of disease prevention and health guarantee for healthy people. After acquiring user detection data, the medical terminal binds and transfers the user detection data and user identity (ID) to the central medical website equipment.

During the implementation of the present invention, the inventors find that in the prior art, when the user detection data is being uploaded to the central medical website equipment, the user detection data is at the risk of being intercepted.

SUMMARY OF THE INVENTION

Embodiments of the present invention provide a method, a device, and a system for remotely acquiring user physiological detection data, so as to enhance the transfer security of the user physiological detection data.

The embodiments of the present invention provide the following technical solutions.

A method for remotely acquiring user physiological detection data includes:
receiving detection related information sent by handheld equipment, in which the detection related information includes user ID information and equipment positioning information;
sending a detection start instruction to corresponding medical detection equipment according to the equipment positioning information;
receiving user physiological detection data sent by the corresponding medical detection equipment, in which the user physiological detection data is associated with an equipment ID of the corresponding medical detection equipment; and
binding and sending the user physiological detection data and the associated user ID information according to associative information of the user ID information and the equipment ID of the medical detection equipment.

A telemedicine system includes medical detection equipment and a detection controller, in which:
the medical detection equipment is configured to receive and execute a control instruction sent by the detection controller, provide a user with a physiological index detection service, and send obtained user physiological detection data to the detection controller; and
the detection controller is configured to receive detection related information, including user ID information and equipment positioning information, sent by handheld equipment, send a detection start instruction to the corresponding medical detection equipment according to the equipment positioning information, and bind and send the user physiological detection data and the associated user ID information according to associative information of the user ID information and an equipment ID, after receiving the user physiological detection data that is associated with the equipment ID and is sent by the medical detection equipment.

A detection controller includes:
a receiving unit, configured to receive detection related information sent by handheld equipment, in which the detection related information includes user ID information and equipment positioning information; and receive user physiological detection data sent by medical detection equipment, in which the user physiological detection data is associated with an equipment ID of the medical detection equipment;
a control unit, configured to send a detection start instruction to corresponding medical detection equipment according to the equipment positioning information; and
a sending unit, configured to bind and send the user physiological detection data and associated user ID information according to associative information of the user ID information and the equipment ID of the medical detection equipment.

In view of the above, according to the embodiments of the present invention, the detection related information sent by the handheld equipment is received, in which the detection related information includes the user ID information and the equipment positioning information; the user physiological detection data sent by the medical detection equipment is received, in which the user physiological detection data is associated with the equipment ID of the medical detection equipment; and the user physiological detection data and the associated user ID information are bound and sent according to the associative information of the user ID information and the equipment ID. Therefore, the user ID information and the user physiological detection data are transferred to the detection controller through different channels respectively, and the detection controller on a network side combines the user ID and the user physiological detection data. The medical detection equipment is only responsible for detection, and does not know which user is detected, thereby preventing the user physiological detection data from being maliciously intercepted during the transfer process initiated by the medical detection equipment, and enhancing the transfer security of the user physiological detection data.

BRIEF DESCRIPTION OF THE DRAWINGS

To illustrate the technical solutions according to the embodiments of the present invention or in the prior art more clearly, the accompanying drawings for describing the embodiments or the prior art are introduced briefly in the following. Apparently, the accompanying drawings in the following description are only about some embodiments of the present invention, and persons of ordinary skill in the art can derive other drawings from the accompanying drawings without creative efforts.

DETAILED DESCRIPTION OF THE EMBODIMENTS

In order to make the objectives, technical solutions, and advantages according to the embodiments of the present invention more clearly, the technical solutions according to the embodiments of the present invention will be clearly and completely described with the accompanying drawings. It is obvious that the embodiments to be described are only a part rather than all of the embodiments of the present invention. All other embodiments obtained by persons of ordinary skill in the art based on the embodiments of the present invention without creative efforts shall fall within the protection scope of the present invention.

Embodiments of the present invention provide a method for remotely acquiring user physiological detection data, a detection controller, and a telemedicine system. User ID information and user physiological detection data are transferred to the detection controller through different channels respectively, and the detection controller on a network side binds and sends the user physiological detection data and an associated user ID to, for example, a data center of the telemedicine system to be stored for a specialist doctor in a city hospital to read and accordingly operate a diagnostic/therapeutic terminal deployed in the city hospital to diagnose conditions of the user. The user ID and the user physiological detection data are combined on the network side, that is, medical detection equipment is only responsible for detection, and does not know which user is detected, so that it is guaranteed that the user physiological detection data is not maliciously intercepted, thereby enhancing the transfer security of the user physiological detection data.

The embodiments of the present invention are described in detail below with reference to the accompanying drawings.

Figure 1:
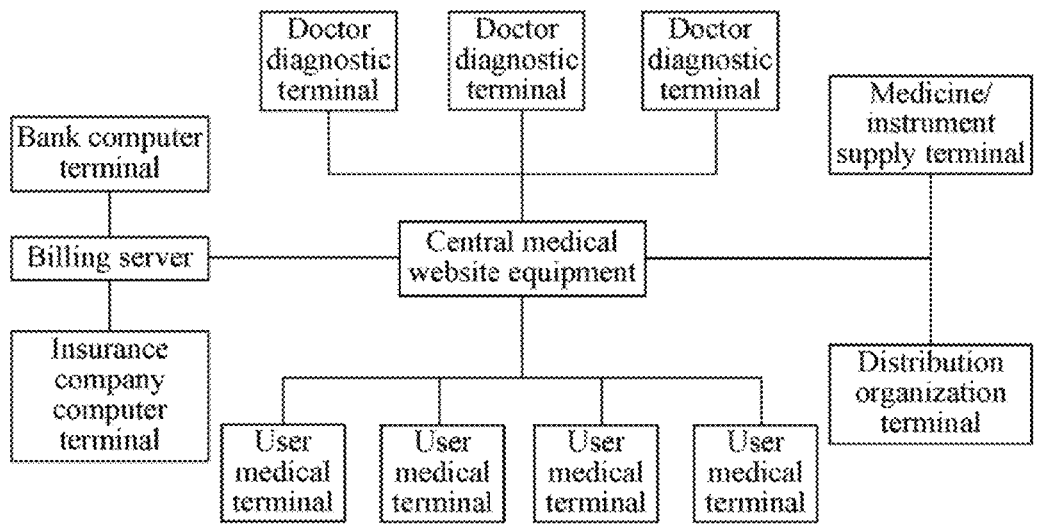
FIG. 1 is a schematic structure diagram of a telemedicine health care system in the prior art.
Figure 2:
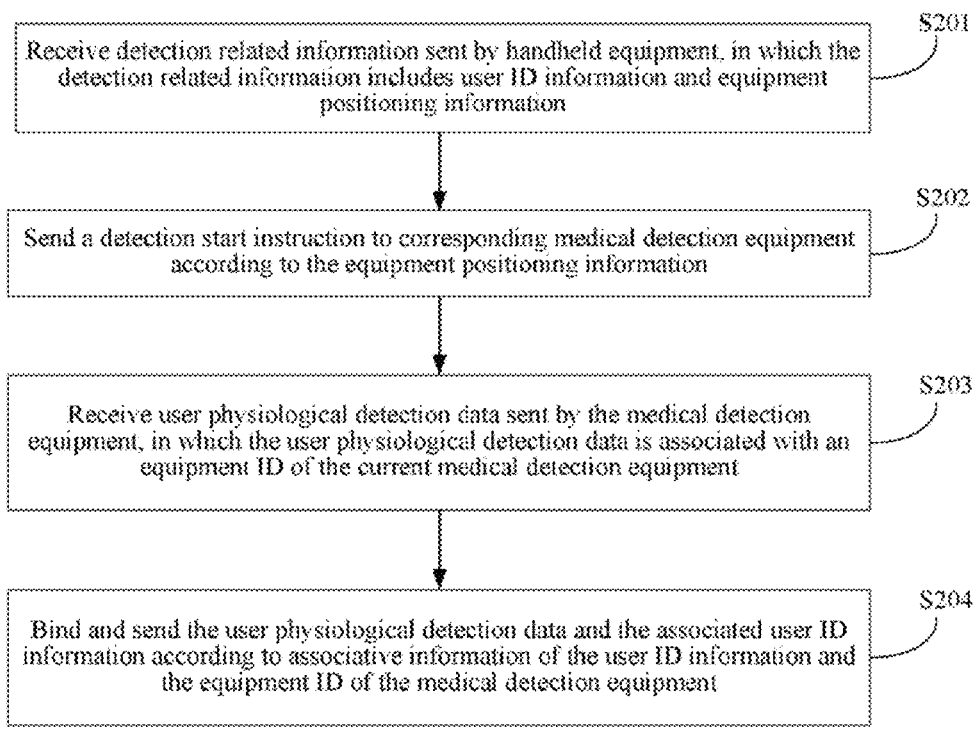
FIG. 2 is a schematic flow chart of a method for remotely acquiring user physiological detection data according to an embodiment of the present invention.

FIG. 2 is a schematic flow chart of a method for remotely acquiring user physiological detection data according to an embodiment of the present invention. An implementation subject of the method may be detection control equipment, deployed on a network side, in a telemedicine system of an embodiment of the present invention, and may also be a network side server in the telemedicine system of an embodiment of the present invention, which is not limited herein. The method may include the following steps.

Step S201: Receive detection related information sent by handheld equipment, in which the detection related information includes user ID information and equipment positioning information.

Specifically, the equipment positioning information may be an equipment ID, and may also be user location information.

The equipment ID is an equipment ID of medical detection equipment, that is, information capable of uniquely identifying the medical detection equipment, and can be manifested by a number or an image, which is not limited herein.

The user ID herein may be acquired in various manners, which may be, for example, the user's mobile phone number, ID card number, social security card number, or medical card number (which is the number of a medical card issued by a hospital, and different medical card numbers can be used to uniquely identify one patient).

Optionally, after the detection control equipment receives the user ID and the equipment positioning information sent by the handheld equipment, if the equipment positioning information is specifically the equipment ID of the medical detection equipment, the detection control equipment may directly associate the user ID with the equipment ID and save the associated user ID and equipment ID.

If the equipment positioning information is the user location information, the detection control equipment further determines the medical detection equipment suitable for a current user according to the user location information and a selection policy, associates the user ID with an equipment ID of the determined medical detection equipment, and saves the associated user ID and equipment ID of the determined medical detection equipment.

It should be noted that, the selection policy herein may be a default policy (for example, selecting the medical detection equipment closest to the current user), or may be a selection policy that is flexibly determined according to an actual application.

The handheld equipment herein may be a mobile phone having special functions, for example, having the function of sending instructions to a detection controller and the function of acquiring a detection equipment ID from the medical detection equipment through a short-distance wireless technology, or having the positioning function, or having the function of scanning a bar code.

Step S202: Send a detection start instruction to corresponding medical detection equipment according to the equipment positioning information, in which the medical detection equipment is indicated by the equipment ID.

Step S203: Receive the user physiological detection data sent by the corresponding medical detection equipment, in which the user physiological detection data is associated with the equipment ID of the corresponding medical detection equipment.

Step S204: Bind and send the user physiological detection data and the associated user ID information according to associative information of the user ID information and the equipment ID.

Specifically, this step may include: determining, by the detection controller, the user ID, which is associated with the user physiological detection data, according to the associated and saved user ID information and equipment ID and the user physiological detection data associated with the equipment ID of the corresponding medical detection equipment, and binding and sending the user physiological detection data and the associated user ID information.

It can be seen that in the method for remotely acquiring user physiological detection data according to the embodiment of the present invention, the user ID information and the user physiological detection data are transferred to the detection controller through different channels respectively, and the detection controller binds and sends the user physiological detection data and the associated user ID to, for example, a data center of a telemedicine system to be stored for a specialist doctor in a city hospital to read and accordingly operate a diagnostic/therapeutic terminal deployed in the city hospital to diagnose conditions of the user. The user ID and the user physiological detection data are combined on the network side, and the medical detection equipment is only responsible for detection, and does not know which user is detected, so as to prevent the user physiological detection data from being maliciously intercepted during the transfer process initiated by the medical detection equipment, thereby enhancing the transfer security of the user physiological detection data.

Figure 3:
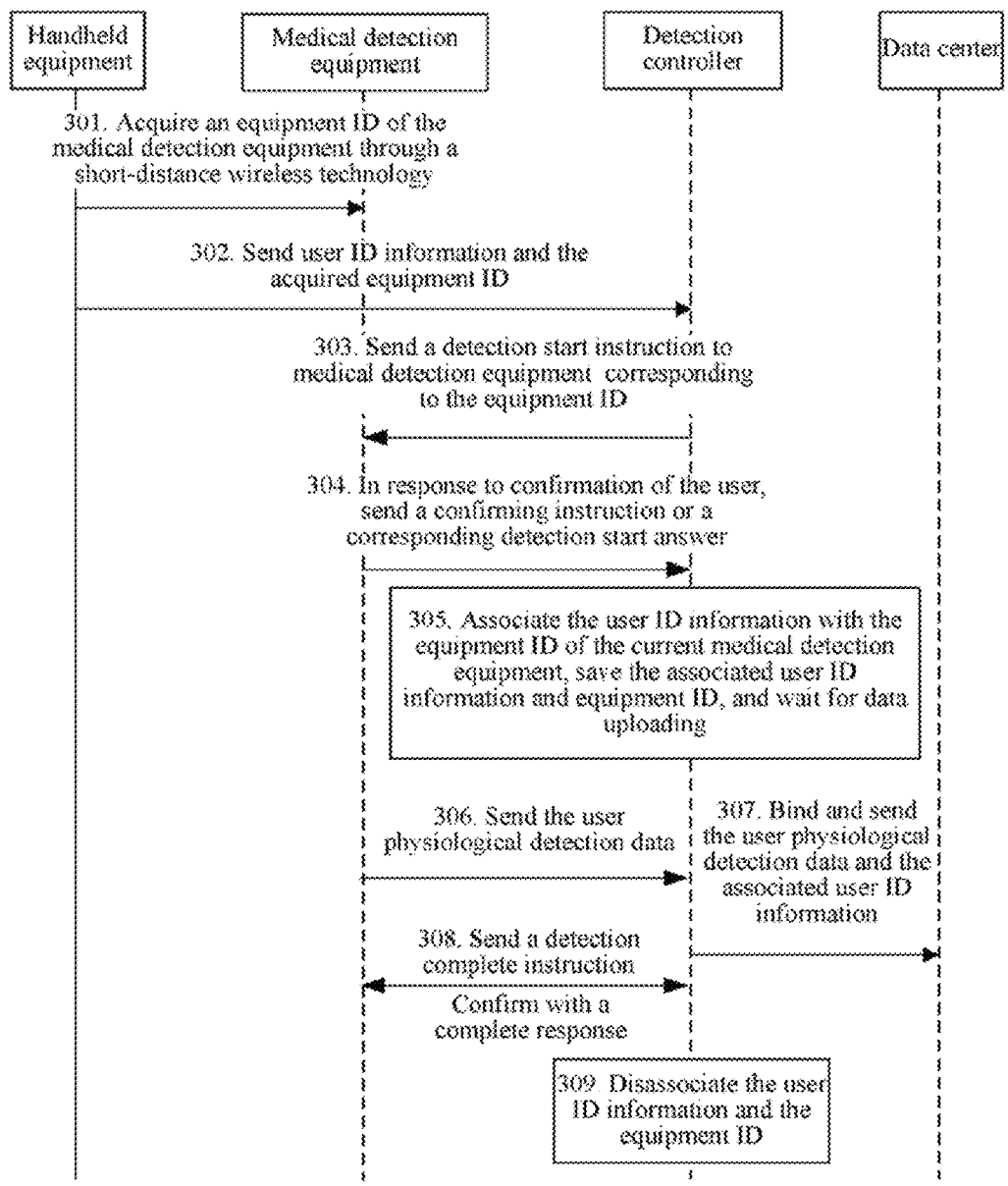
FIG. 3 is a schematic interaction diagram of a method for remotely acquiring user physiological detection data according to an embodiment of the present invention, which is applied in a telemedicine system shown in FIG. 4.
Figure 4:
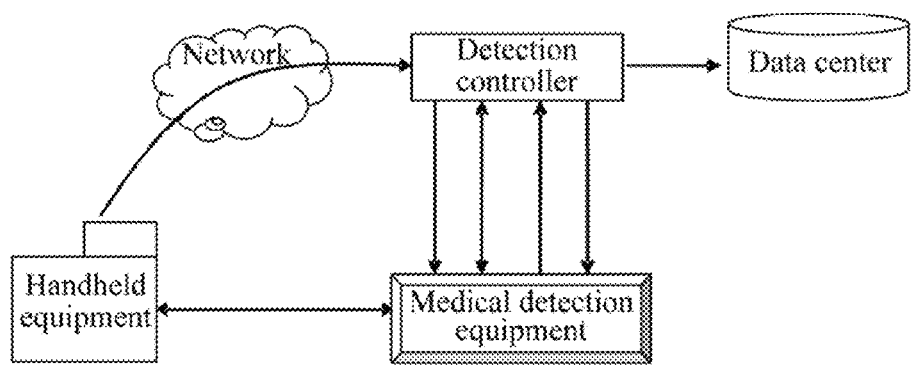
FIG. 4 is a schematic structure diagram of a telemedicine system according to an embodiment of the present invention.

FIG. 3 is a schematic interaction diagram of a method for remotely acquiring user physiological detection data according to an embodiment of the present invention, which is applied in a telemedicine system shown in FIG. 4. In this embodiment, equipment positioning information is specifically an equipment ID of medical detection equipment. The method specifically includes the following steps.

Step S301: A user holding handheld equipment approaches medical detection equipment, and acquires an equipment ID of the medical detection equipment through a short-distance wireless technology.

Step S302: The handheld equipment sends user ID information and the acquired equipment ID to a detection controller.

Step S303: After receiving the sent user ID information and equipment ID, the detection controller verifies the user ID information (optional), and sends a detection start instruction to corresponding medical detection equipment according to the equipment ID after the verification of the user ID is passed.

Specifically, the detection controller verifies validation of the user ID at least according to a matching result between user ID information saved on a network side and the received user ID information, provides a service if the current user is a valid user, and denies the service if the current user is an invalid user. The method may include: when the received user ID information matches the user ID information saved on the network side, determining whether the user is a valid user according to service registration information of the matching user, and when the received user ID information does not match any user ID information saved on the network side, determining the user as an invalid user.

The user ID information may be acquired in various manners, which may be, for example, the user's mobile phone number, ID card number, social security card number, or medical card number (which is the number of a medical card issued by a hospital, and different medical card numbers can be used to uniquely identify one patient). The following description is provided by using an example in which the user ID information is the social security card number.

When the received social security card number matches a social security card number of a user in a data center, it is determined whether the user is a valid user according to service registration information of the matching user. If the user is determined as a valid user, the service is provided, and if the user is determined as an invalid user, the service is denied or an error is reported.

When the received social security card number does not match any user's social security card number in the data center, the user is determined as an invalid user, and the service is denied or an error is reported.

Step S304: After receiving the detection start instruction, the medical detection equipment prompts the corresponding user to start detection, and in response to confirmation of the user (specifically, the user clicks a confirmation key or button on the medical detection equipment, and the medical detection equipment responds to the key-clicking or button-clicking action of the user), sends a confirming instruction or a corresponding detection start answer to the detection controller.

Step S305: The detection controller associates the user ID information with the equipment ID of the medical detection equipment, saves the associated user ID information and equipment ID of the medical detection equipment, and waits for the medical detection equipment to upload detection data. It should be noted that, in step S303, after the verification of the user ID is passed, an optional method may include: associating the received user ID information with the equipment ID, and saving the associated user ID information and equipment ID; in this way, step S305 can be omitted.

Step S306: The user uses the medical detection equipment to detect physiological indexes, and after the detection is completed, the medical detection equipment sends user physiological detection data to the detection controller. It should be noted that, when sending the user physiological detection data, the medical detection equipment sends the user physiological detection data associated with the equipment ID of the medical detection equipment. In other words, the user physiological detection data herein is associated with the equipment ID of the medical detection equipment.

Specifically, the medical detection equipment herein may include, but is not limited to, an electrocardiographic detection sensor, a blood pressure detection sensor, a blood glucose detection sensor, and a urine glucose detection sensor. Accordingly, the user physiological detection data includes, but is not limited to, an electrocardiogram, a cardiac rhythm; a blood pressure, and other physiological parameters.

Step S307: The detection controller determines the user ID information, which is associated with the received user physiological detection data, according to associative information of the user ID information and the equipment ID in step S305, and binds and sends the user physiological detection data and the associated user ID information to the data center.

Step S308 to step S309: The detection controller sends a detection complete instruction to the medical detection equipment, and after the medical detection equipment confirms that the detection process is completed, the detection controller disassociates the user ID information and the equipment ID. The current process ends.

It should be noted that, besides the method provided in this embodiment, in an implementation, if the medical detection equipment is equipment having a bar code, step S301 in this embodiment may be replaced with: scanning, by the handheld equipment (having the function of scanning a bar code), bar code image information of the medical detection equipment, acquiring the equipment ID by analyzing the bar code image information of the equipment, and sending to the detection controller the user ID information and the equipment ID that is acquired by converting the bar code image information of the equipment.

In another implementation, if the medical detection equipment is equipment having a two-dimensional code, step S301 in this embodiment may be replaced with: scanning, by the handheld equipment (having the function of scanning a two-dimensional code), two-dimensional code image information of the medical detection equipment, acquiring the equipment ID by analyzing the two-dimensional code image information of the equipment, and sending to the detection controller the user ID information and the equipment ID that is acquired by converting the two-dimensional code image information.

In further another implementation, if the medical detection equipment is equipment having a radio frequency identification (RFID), step S301 in this embodiment may be replaced with: scanning, by the handheld equipment (having the function of scanning an RFID), RFID information of the medical detection equipment, acquiring the equipment ID by analyzing the RFID information of the equipment, and sending to the detection controller the user ID information and the equipment ID that is acquired by converting the RFID information of the equipment.

It can be seen that in the method for remotely acquiring user physiological detection data according to the embodiment of the present invention, the user ID information and the user physiological detection data are transferred to the detection controller through different channels respectively, and the detection controller binds and sends the user physiological detection data and the associated user ID to, for example, a data center of a telemedicine system to be stored for a specialist doctor in a city hospital to read and accordingly operate a diagnostic/therapeutic terminal deployed in the city hospital to diagnose conditions of the user. The user ID and the user physiological detection data are combined on the network side, and the medical detection equipment is only responsible for detection, and does not know which user is detected, so as to prevent the user physiological detection data from being maliciously intercepted during the transfer process initiated by the medical detection equipment, thereby enhancing the transfer security of the user physiological detection data.

In addition, the detection controller binds and sends the user physiological detection data and the associated user ID information to a transfer path of the data center. The detection controller and the data center are both on the network side, for example, both deployed in a machine room of the city hospital, which belongs to a controllable transfer path, highly secure, and less likely to be intercepted.

Furthermore, in the embodiment of the present invention, the user ID information is separated from the medical detection equipment, thereby realizing the sharing of the medical detection equipment.

Figure 5:
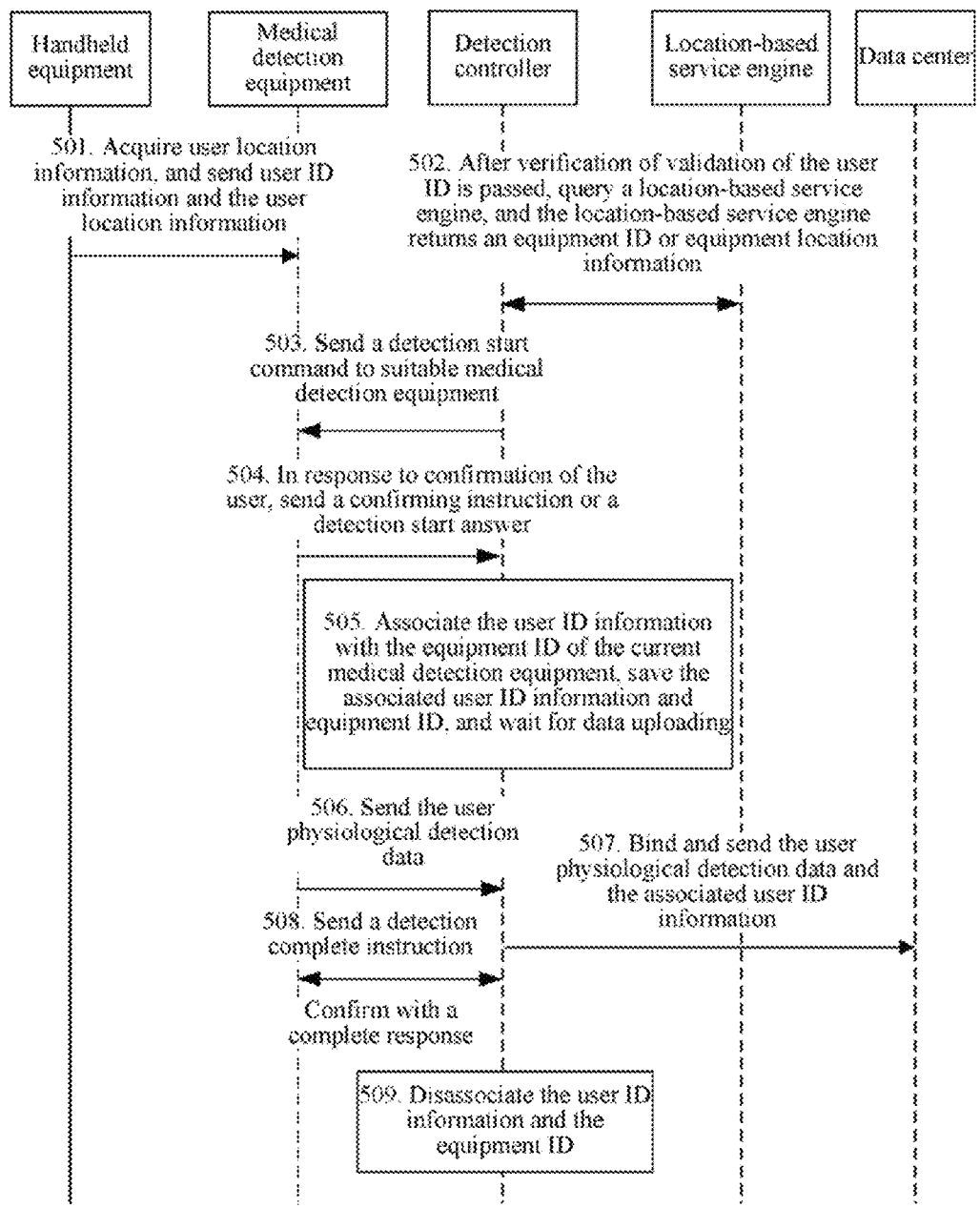
FIG. 5 is a schematic interaction diagram of a method for remotely acquiring user physiological detection data according to an embodiment of the present invention, which is applied in a telemedicine system shown in FIG. 6.
Figure 6:
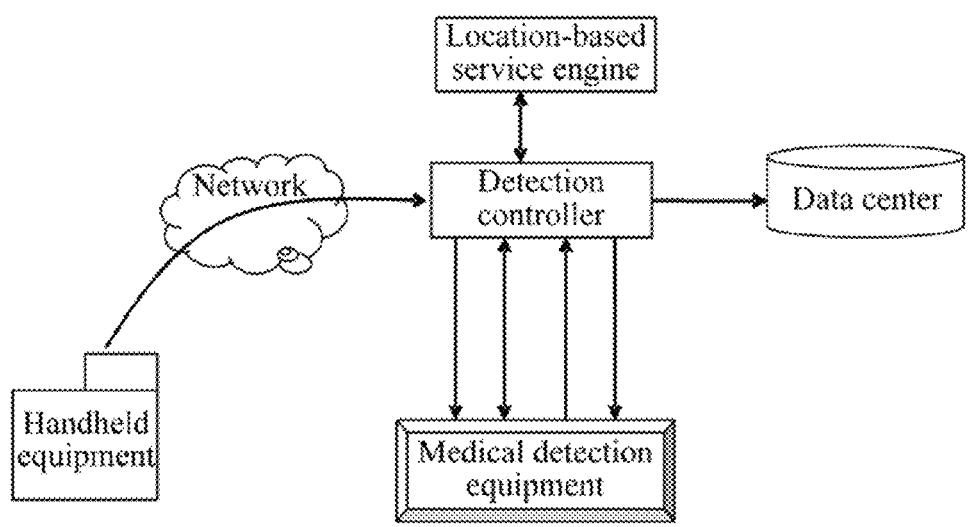
FIG. 6 is a schematic structure diagram of another telemedicine system according to an embodiment of the present invention.

FIG. 5 is a schematic interaction diagram of a method for remotely acquiring user physiological detection data according to an embodiment of the present invention, which is applied in a telemedicine system shown in FIG. 6. In this embodiment, equipment positioning information is specifically user location information, and the method specifically includes the following steps.

Step S501: A user holding handheld equipment approaches medical detection equipment, and the handheld equipment acquires location information of the handheld equipment (that is, user location information) through a positioning module, and sends user ID information and the user location information to a detection controller.

Step S502: After verification of validation of the user ID is passed, the detection controller queries a location-based service engine, and the location-based service engine determines suitable medical detection equipment (manifested by an equipment ID or equipment location information of the medical detection equipment) according to the user location information and a selection policy.

Specifically, the selection policy may be selecting medical detection equipment within a preset range of a user location or closest to the current user location to provide the service (in one implementation, the policy may be used by default as a default selection policy); may also be selecting medical detection equipment that is within a preset range of the user location or closest to the current user location and is suitable for a user service level (users of different levels use medical detection equipment of different levels); and may also be selecting medical detection equipment that is within a preset range of the user location or closest to the current user location and is suitable for a user requested service type (users requesting different service types use medical detection equipment of different types). The present invention is not limited thereto, and the selection policy may be flexibly determined according to an actual application.

Step S503: The detection controller sends a detection start instruction to the determined medical detection equipment. Specifically, the detection controller sends the detection start instruction to the determined medical detection equipment according to the equipment ID or the equipment location information of the medical detection equipment.

The sending the detection start instruction to the determined medical detection equipment according to the equipment ID or the equipment location information of the medical detection equipment may include: sending the detection start instruction to the medical detection equipment to which the equipment location information is directed, according to the equipment location information included in the equipment ID; or sending the detection start instruction to the medical detection equipment to which the equipment location information associated with the equipment ID is directed, according to associative information of the equipment ID and the equipment location information; and alternatively, returning to the handheld equipment of the user the location information of the medical detection equipment providing the service.

Step S504: After receiving the detection start instruction, the medical detection equipment prompts the corresponding user to start detection, and in response to confirmation of the user (specifically, the user clicks a confirmation key or button on the medical detection equipment, and the medical detection equipment responds to the key-clicking or button-clicking action of the user), sends a confirming instruction or a corresponding detection start answer to the detection controller.

Step S505: The detection controller associates the user ID information with the equipment ID of the medical detection equipment determined in step S502, saves the associated user ID information and equipment ID of the medical detection equipment determined in step S502, and waits for the medical detection equipment to upload detection data.

Step S506: The user uses the medical detection equipment to detect physiological indexes, and after the detection is completed, the medical detection equipment sends user physiological detection data to the detection controller. It should be noted that, when the medical detection equipment sends the user physiological detection data, the medical detection equipment sends the user physiological detection data associated with the equipment ID of the medical detection equipment. In other words, the user physiological detection data herein is associated with the equipment ID of the medical detection equipment.

Step S507: The detection controller determines the user ID information, which is associated with the received user physiological detection data; according to associative information of the user ID information and the equipment ID in step S505, and binds and sends the user physiological detection data and the associated user ID information to a data center.

Step S508 to step S509: The detection controller sends a detection complete instruction to the medical detection equipment, and after the medical detection equipment confirms that the detection process is completed, the detection controller disassociates the user ID information and the equipment ID. The current process ends.

It can be seen that in the method for remotely acquiring user physiological detection data according to the embodiment of the present invention, the user ID information and the user physiological detection data are transferred to the detection controller through different channels respectively, and the detection controller binds and sends the user physiological detection data and the associated user ED to, for example, a data center of a telemedicine system to be stored for a specialist doctor in a city hospital to read and accordingly operate a diagnostic/therapeutic terminal deployed in the city hospital to diagnose conditions of the user. The user ID and the user physiological detection data are combined on the network side, and the medical detection equipment is only responsible for detection, and does not know which user is detected, so as to prevent the user physiological detection data from being maliciously intercepted during the transfer process initiated by the medical detection equipment, thereby enhancing the transfer security of the user physiological detection data.

In addition, the detection controller binds and sends the user physiological detection data and the associated user ID information to a transfer path of the data center. The detection controller and the data center are both on the network side, for example, both deployed in a machine room of the city hospital, which belongs to a controllable transfer path, highly secure, and less likely to be intercepted.

Furthermore, in the embodiment of the present invention, the user ID information is separated from the medical detection equipment, thereby realizing the sharing of the medical detection equipment.

Figure 7:
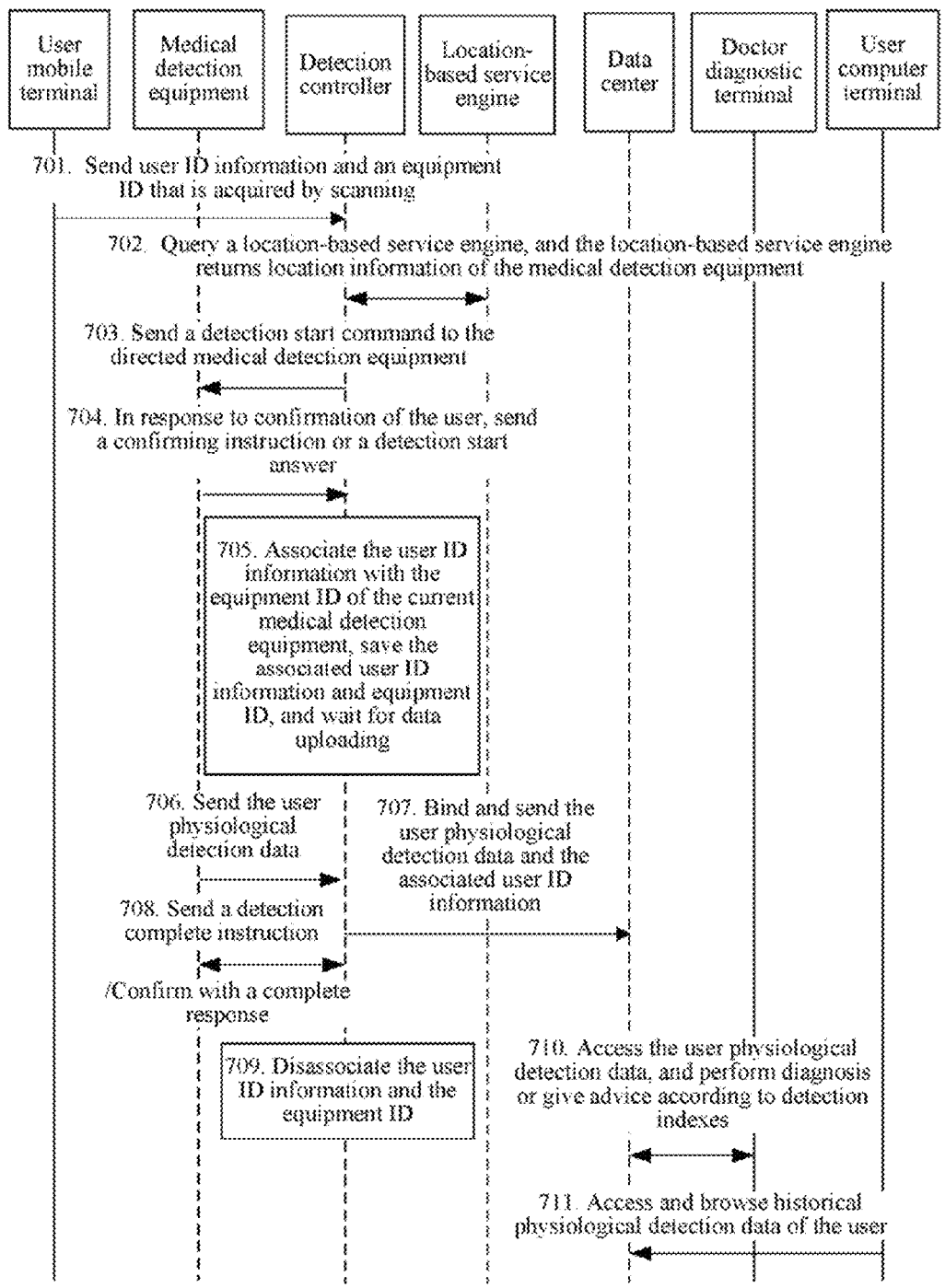
FIG. 7 is a schematic interaction diagram of a method for remotely acquiring user physiological detection data according to an embodiment of the present invention, which is applied in a telemedicine system shown in FIG. 8.
Figure 8:
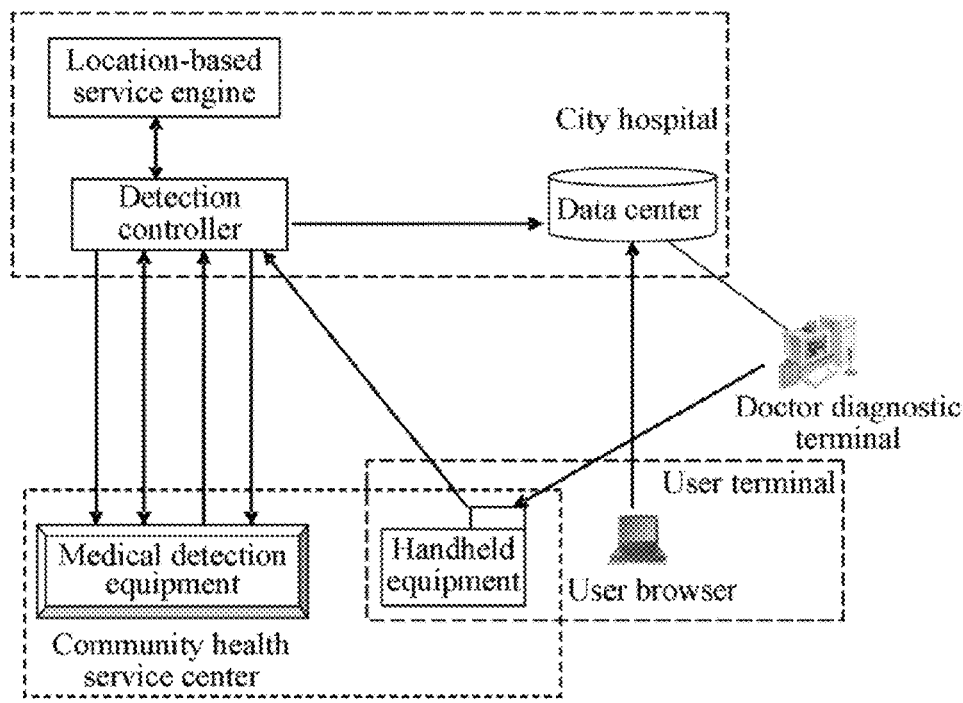
FIG. 8 is a schematic structure diagram of still another telemedicine system according to an embodiment of the present invention.

FIG. 7 is a schematic interaction diagram of a method for remotely acquiring user physiological detection data in a specific application scenario, which is applied in a telemedicine system shown in FIG. 8. In this embodiment, equipment positioning information is specifically an equipment ID of medical detection equipment, the medical detection equipment is deployed in community heath service centers of a city hospital distributed in communities, a detection controller and a data center are deployed in a machine room of the city hospital, and the method specifically includes the following steps.

Step S701: A user enters a community health service center, and uses a user mobile terminal (for example, a mobile phone) to scan bar code image information of medical detection equipment deployed in the community health service center. The user mobile terminal sends user ID information (for example, a social security card number) and a corresponding equipment ID (that is, during the scanning, the bar code image information is converted into the corresponding equipment ID) to the detection controller.

Step S702: The detection controller queries a location-based service engine, and the location-based service engine determines location information (in this embodiment, the location information of the detection equipment may specifically be a number of a subscriber identity module (SIM) card built in the medical detection equipment) according to the equipment ID.

Step S703: The detection controller sends a detection start instruction to the medical detection equipment to which the location information (for example, the number of the SIM card) acquired in step S702 is directed.

Step S704: After receiving the detection start instruction, the medical detection equipment prompts the corresponding user to start detection, and in response to confirmation of the user (specifically, the user clicks a confirmation key or button on the medical detection equipment, and the medical detection equipment responds to the key-clicking or button-clicking action of the user), sends a confirming instruction or a corresponding detection start answer to the detection controller.

Step S705: The detection controller associates the user ID information with the equipment ID of the medical detection equipment, saves the associated user ID information and equipment ID of the medical detection equipment, and waits for the medical detection equipment to upload detection data.

It should be noted that, in step S704, if the user does not feed back any confirmation within a preset time range, the detection controller automatically cancels the detection process. The preset time range may be flexibly determined according to an actual application.

Step S706: The user uses the medical detection equipment to detect physiological indexes, and after the detection is completed, the medical detection equipment sends user physiological detection data to the detection controller through a network. It should be noted that, when the medical detection equipment sends the user physiological detection data, the medical detection equipment sends the user physiological detection data associated with the equipment ID of the medical detection equipment. In other words, the user physiological detection data herein is associated with the equipment ID of the medical detection equipment.

Step S707: The detection controller determines the user ID information, which is associated with the received user physiological detection data, according to associative information of the user ID information and the equipment ID in step S705, and binds and sends the user physiological detection data and the associated user ID information to the data center.

Step S708 to step S709: The detection controller sends a detection complete instruction to the medical detection equipment, and after the medical detection equipment confirms that the detection process is completed, the detection controller disassociates the user ID information and the equipment ID.

Step S710: A medical specialist of the city hospital accesses the user physiological detection data through a doctor diagnostic terminal (a computer terminal), and performs diagnosis or gives advice according to detection indexes, and the doctor diagnostic terminal sends a diagnostic result or advice to the corresponding user mobile terminal through a wireless communication network. It should be noted that, if the user subscribes a physiological index trend chart, a back-end server of the city hospital returns the subscription content to the user terminal periodically.

Step S711: The user accesses the data center of the city hospital (the back-end server of the city hospital, not shown) through a computer terminal, and browses historical physiological detection data of the user. Besides, the user may also browse a historical trend chart of each of the physiological indexes. This step is optional.

It should be noted that, functions of the location-based service engine and functions of the detection controller in this embodiment may be integrated. In other words, an integrated detection controller also has the location-based service functions.

It can be seen that in the method for remotely acquiring user physiological detection data according to the embodiment of the present invention, the user ID information and the user physiological detection data are transferred to the detection controller through different channels respectively, and the detection controller binds and sends the user physiological detection data and the associated user ID to, for example, a data center of a telemedicine system to be stored for a specialist doctor in a city hospital to read and accordingly operate a diagnostic/therapeutic terminal deployed in the city hospital to diagnose conditions of the user. The user ID and the user physiological detection data are combined on the network side, and the medical detection equipment is only responsible for detection, and does not know which user is detected, so as to prevent the user physiological detection data from being maliciously intercepted during the transfer process initiated by the medical detection equipment, thereby enhancing the transfer security of the user physiological detection data.

In addition, the detection controller binds and sends the user physiological detection data and the associated user ID information to a transfer path of the data center. The detection controller and the data center are both on the network side, for example, both deployed in a machine room of the city hospital, which belongs to a controllable transfer path, highly secure, and less likely to be intercepted.

Furthermore, in the embodiment of the present invention, the user ID information is separated from the medical detection equipment, thereby realizing the sharing of the medical detection equipment.

Figure 9:
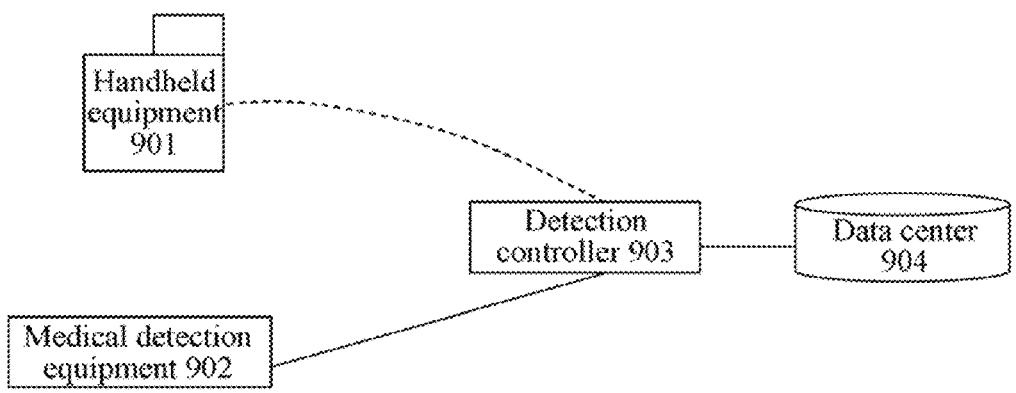
FIG. 9 is a schematic structure diagram of a telemedicine system according to an embodiment of the present invention.

As shown in FIG. 9, an embodiment of the present invention provides a telemedicine system, which may include medical detection equipment 902 and a detection controller 903.

The medical detection equipment 902 is configured to receive and execute a control instruction sent by the detection controller 903, provide a user with a physiological index detection function, and send obtained user physiological detection data to the detection controller 903.

The detection controller 903 is configured to receive detection related information, including user ID information and equipment positioning information, sent by handheld equipment, send a detection start instruction to the corresponding medical detection equipment 902 according to the equipment positioning information, and after receiving the user physiological detection data that is associated with the equipment ID and is sent by the medical detection equipment 902, bind and send the user physiological detection data and the associated user ID information according to associative information of the user ID information and the equipment ID.

Furthermore, the detection controller 903 is further configured to verify validation of the user ID, send the detection start instruction to the corresponding medical detection equipment 902 according to the equipment positioning information after the verification of the validation of the ID is passed, associate the user ID information with the equipment ID of the medical detection equipment, and save the associated user ID information and the equipment ID of the medical detection equipment (if the received equipment positioning information is the equipment ID, the associating and saving process is directly performed; while if the received equipment positioning information is user location information, the user ID information and the equipment ID that is acquired according to the user location information are associated and saved).

In one implementation, the equipment positioning information is the equipment ID, and accordingly, the medical detection equipment 902 is further configured to receive and respond to a request sent by the handheld equipment 901 for acquiring the equipment ID.

The detection controller 903 is specifically configured to send the detection start instruction to the medical detection equipment to which the equipment location information associated with the equipment ID is directed, according to associative information of the equipment ID and equipment location information (the associative information herein may be pre-saved or dynamically acquired); or is specifically configured to send the detection start instruction to the medical detection equipment to which the equipment location information is directed, according to the equipment location information included in the equipment ID.

In another implementation, the equipment positioning information is the user location information. Accordingly, the detection controller 903 is specifically configured to output the user location information to a location-based service engine 905 (not shown) after the verification of the validation of the user ID is passed, receive the equipment ID or the equipment location information returned by the location-based service engine 905, and send the detection start instruction to the corresponding medical detection equipment according to the equipment ID or the equipment location information. Specifically, lithe location-based service engine 905 returns the equipment ID, the detection controller 903 is specifically configured to send the detection start instruction to the medical detection equipment to which the equipment location information associated with the received equipment ID is directed, according to preset associative information of the equipment ID and the equipment location information; or is specifically configured to send the detection start instruction to the medical detection equipment to which the equipment location information is directed, according to the equipment location information included in the equipment ID.

Accordingly, the system of the embodiment of the present invention further includes the location-based service engine 905, configured to determine suitable medical detection equipment according to the user location information and a selection policy, and return the equipment ID of the suitable medical detection equipment or the equipment location information of the medical detection equipment (for example, a number of an SIM card built in the medical detection equipment) to the detection controller 903. It should be noted that the location-based service function may also be integrated in the detection controller.

Specifically, the selection policy may be selecting medical detection equipment within a preset range of a user location or closest to the current user location to provide the service (the policy may be a default selection policy); may also be selecting medical detection equipment that is within a preset range of the user location or closest to the current user location and is suitable for a user service level (users of different levels use medical detection equipment of different levels); and may also be selecting medical detection equipment that is within a preset range of the user location or closest to the current user location and is suitable for a user requested service type (users requesting different service types use medical detection equipment of different types). The present invention is not limited thereto, and the selection policy may be flexibly determined according to an actual application.

In another implementation manner, if the equipment positioning information is the equipment ID, the detection controller 903 is specifically configured to output the equipment ID to the location-based service engine after the verification of the validation of the user ID is passed, receive the equipment location information returned by the location-based service engine, and send the detection start instruction to the corresponding medical detection equipment according to the equipment location information.

The system further includes the location-based service engine 905, configured to acquire the equipment location information of the corresponding medical detection equipment according to the equipment ID.

Furthermore, the telemedicine system of the embodiment of the present invention may further include:

a data center 904, configured to associate the user physiological detection data with the user ID information which are sent by the detection controller 903, and save the associated user physiological detection data and user ID information.

Specifically, the data center 904 provides the detection controller 903 with an interface for saving data.

Furthermore, the telemedicine system of the embodiment of the present invention may further include the handheld equipment 901, configured to communicate with the detection controller 903, and send the detection related information to the detection controller 903. The detection related information includes the user ID information and the equipment positioning information.

In an implementation manner, the handheld equipment 901 is capable of acquiring the equipment ID from the medical detection equipment through a short-distance wireless technology. In another implementation manner, the handheld equipment 901 has a positioning function (for example, positioning through a global positioning system (GPS), or mobile base stations). In another implementation manner, the handheld equipment 901 may have a function of scanning a bar code (or a two-dimensional code or an RFID), and acquire the equipment ID of the medical detection equipment by analyzing bar code image information, or two-dimensional code image information, or RFID information of the equipment.

It should be noted that, the medical detection equipment involved in the embodiment of the present invention may be deployed in a distributed mode, for example, deployed in community health service centers, and the detection controller may be deployed in the headquarter of a city hospital (for example, in a machine room of the hospital), so that it is convenient for a user in a community to adopt the solution according to the embodiment of the present invention to remotely send user physiological detection data to the data center of the city hospital. In addition, during the sending of the user physiological detection data, the user ID information and the user physiological detection data are transferred to the detection controller through different channels respectively, and the detection controller binds and sends the user physiological detection data and the associated user ID to, for example, a data center of a telemedicine system to be stored for a specialist doctor in a city hospital to read and accordingly operate a diagnostic/therapeutic terminal deployed in the city hospital to diagnose conditions of the user. The user ID and the user physiological detection data are combined on the network side, and the medical detection equipment is only responsible for detection, and does not know which user is detected, so as to prevent the user physiological detection data from being maliciously intercepted during the transfer process initiated by the medical detection equipment, thereby enhancing the transfer security of the user physiological detection data.

In addition, the detection controller binds and sends the user physiological detection data and the associated user ID information to a transfer path of the data center. The detection controller and the data center are both on the network side, for example, both deployed in a machine room of the city hospital, which belongs to a controllable transfer path, highly secure, and less likely to be intercepted.

Furthermore, in the embodiment of the present invention, the user ID information is separated from the medical detection equipment, thereby realizing the sharing of the medical detection equipment.

Figure 10:
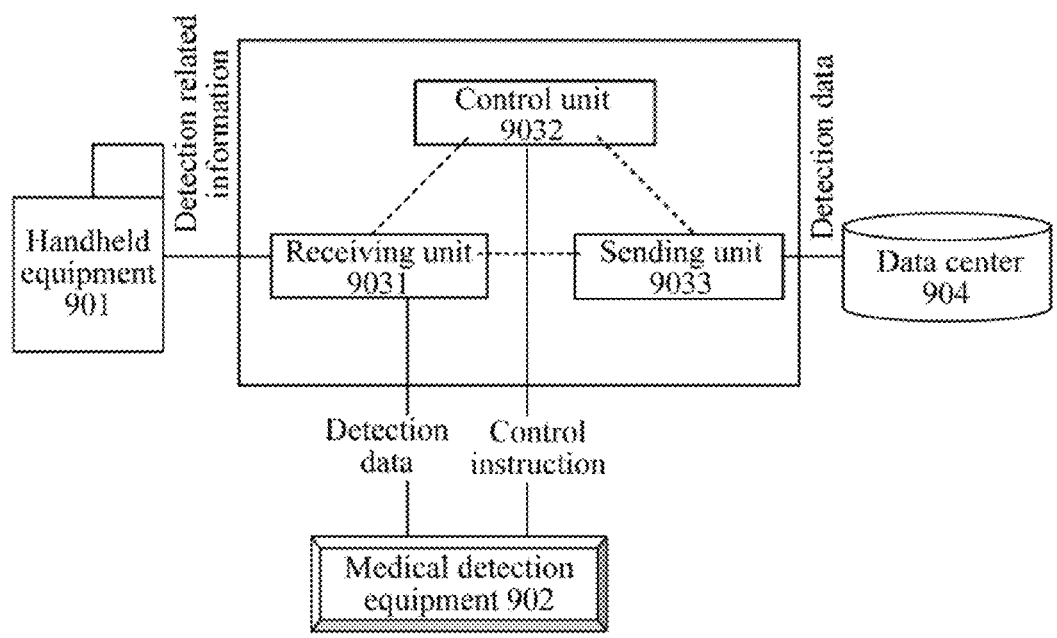
FIG. 10 is a schematic structure diagram of a detection controller according to an embodiment of the present invention.

FIG. 10 is a schematic structure diagram of a detection controller according to an embodiment of the present invention, which can be applied in a telemedicine system. As shown in FIG. 10, the detection controller according to the embodiment of the present invention may include.

A receiving unit 9031, which is configured to receive the detection related information sent by the handheld equipment 901, in which the detection related information includes the user ID information and the equipment positioning information; and receive the user physiological detection data sent by the medical detection equipment 902, in which the user physiological detection data is associated with the equipment ID of the medical detection equipment 902.

Specifically, the detection related information herein may further include information indicating usage of the information to the detection control equipment, for example, BD. The equipment positioning information may be the equipment ID or the user location information. The equipment ID herein is information capable of uniquely identifying the medical detection equipment. The user ID herein may be acquired in various manners, which may be, for example, the user's mobile phone number, ID card number, social security card number, or medical card number (which is the number of a medical card issued by a hospital, and different medical card numbers can be used to uniquely identify one patient).

A control unit 9032, which is configured to send a detection start instruction to the corresponding medical detection equipment 902 according to the equipment positioning information. The medical detection equipment is manifested by the equipment ID.

A sending unit 9033, which is configured to bind and send the user physiological detection data and the associated user ID information according to associative information of the user ID information and the equipment ID. In one implementation, the sending unit 9033 is specifically configured to determine the user ID, which is associated with the user physiological detection data, according to the associated and saved user ID information and equipment ID and the user physiological detection data associated with the equipment ID of the medical detection equipment 902, and bind and send the user physiological detection data and the associated user ID information. As shown in FIG. 10, specifically, the user physiological detection data and the associated user ID information may be sent to the data center 904.

In one implementation, if the equipment positioning information is the equipment ID of the medical detection equipment, the control unit 9032 is a first control unit, configured to, after verification of validation of the user ID is passed, send the detection start instruction to the medical detection equipment to which the equipment location information associated with the equipment ID is directed, according to associative information of the equipment ID and the equipment location information; or send the detection start instruction to the medical detection equipment to which the equipment location information is directed, according to the equipment location information included in the equipment ID.

In another implementation, if the equipment positioning information is the user location information, the control unit 9032 is a second control unit, configured to output the user location information to the location-based service engine after the verification of the validation of the user ID is passed, receive the equipment ID or the equipment location information (for example, a number of an SIM card built in the medical detection equipment) returned by the location-based service engine, and send the detection start instruction to the corresponding medical detection equipment according to the equipment ID or the equipment location information. Specifically, if the location-based service engine returns the equipment ID, the detection controller 903 is specifically configured to send the detection start instruction to the medical detection equipment to which the equipment location information associated with the received equipment ID is directed, according to the preset associative information of the equipment ID and the equipment location information; or is specifically configured to send the detection start instruction to the medical detection equipment to which the equipment location information is directed, according to the equipment location information included in the equipment ID.

The user ID information may be acquired in various manners, which may be, for example, the user's mobile phone number, ID card number, social security card number, or medical card number (which is the number of a medical card issued by a hospital, and different medical card numbers can be used to uniquely identify one patient), and the verification process of the validation of the user ID is described by using an example in which the user ID information is the social security card number.

When the received social security card number matches a social security card number of a user in the data center, it is determined whether the user is a valid user according to service registration information of the user. If the user is determined as a valid user, the service is provided, and if the user is determined as an invalid user, the service is denied or an error is reported.

When the received social security card number does not match any user's social security card number in the data center, the user is determined as an invalid user, and the service is denied or an error is reported.

In another implementation, if the equipment positioning information is the user location information, the control unit 9032 is a third control unit, configured to acquire the equipment ID or the equipment location information of the suitable medical detection equipment according to the user location information and a selection policy after the verification of the validation of the user ID is passed, and send the detection start instruction to the corresponding medical detection equipment according to the equipment ID or the equipment location information. Reference may be made to the aforementioned embodiments for details of the selection policy.

Furthermore, the detection controller of the embodiment of the present invention may further include a storage unit 9034 (not shown), configured to associate the user ID information with the equipment ID and save the associated user ID information and equipment ID.

Accordingly, the control unit 9032 is further configured to associate the user ID received by the receiving unit with the equipment ID acquired by converting the equipment positioning information, and save the associated user ID and equipment ID in the storage unit; or associate the user ID with the equipment ID which are received by the receiving unit, and save the associated user ID and equipment ID in the storage unit.

Specifically, after receiving the user ID and the equipment positioning information that are sent by the handheld equipment, the control unit 9032 may directly associate the user ID with the equipment ID and save the associated user ID and equipment ID, if the equipment positioning information is specifically the equipment ID of the medical detection equipment.

If the equipment positioning information is the user location information, the control unit 9032 further determines medical detection equipment suitable for the current user according to the user location information and a selection policy (for example, a default selection policy or a selection policy flexibly determined according to an actual application), associates the user ID with an equipment ID of the determined medical detection equipment, and saves the associated user ID and equipment ID of the determined medical detection equipment.

The units of the device according to the embodiment of the present invention may be integrated as a whole or deployed in a separated manner. The units may be combined into one unit, and may also be further divided into multiple subunits.

The descriptions of the methods according to the embodiments can be referred to for specific realization of the functional units.

It can be seen that in the detection controller according to the embodiment of the present invention, the user ID information and the user physiological detection data are transferred to the detection controller through different channels respectively, and the detection controller binds and sends the user physiological detection data and the associated user ID to, for example, a data center of a telemedicine system to be stored for a specialist doctor in a city hospital to read and accordingly operate a diagnostic/therapeutic terminal deployed in the city hospital to diagnose conditions of the user. The user ID and the user physiological detection data are combined on the network side, and the medical detection equipment is only responsible for detection, and does not know which user is detected, so as to prevent the user physiological detection data from being maliciously intercepted during the transfer process initiated by the medical detection equipment, thereby enhancing the transfer security of the user physiological detection data.

It should be noted that, the expression of first, second, and third used in the descriptions of the embodiments is not intended to limit a sequence, but only for convenience of distinguishing.

It should be noted that, in the embodiments of the present invention, besides acquiring the equipment ID of the medical detection equipment through the short-distance wireless technology and acquiring the equipment ID of the medical detection equipment by scanning the bar code, the two-dimensional code, or the RFID of the medical detection equipment, the handheld equipment may also adopt a magnetic card identification manner.

Persons of ordinary skill in the art should understand that all or a part of the steps of the method according to the embodiments of the present invention may be implemented by a computer program instructing relevant hardware. The program may be stored in a computer readable storage medium. When the program runs, the steps of the method according to the embodiments of the present invention are performed. The storage medium may be a magnetic disk, an optical disk, a read-only memory (ROM), or a random access memory (RAM).

The descriptions above are only specific embodiments of the present invention. It should be noted that for persons of ordinary skill in the art, improvements and variations may be made without departing from the principle of the present invention, which shall be construed as falling within the protection scope of the present invention.

What is claimed is:

1. A method for remotely acquiring user physiological detection data, comprising:
receiving, by a detection controller on a network side, detection related information sent by handheld equipment through a first channel to a detection controller, wherein the detection related information comprises user identity (ID) information and equipment positioning information;
sending, by the detection controller on the network side, a detection start instruction from the detection controller to corresponding medical detection equipment according to the equipment positioning information;
receiving, by the detection controller on the network side, user physiological detection data sent by the corresponding medical detection equipment through a second channel to the detection controller, wherein the first channel that receives the user ID information and the second channel that receives the user physiological detection data are different communication channels that each transfers data to the detection controller, wherein the first channel comprises a network channel that transfers the user ID information to the detection controller over a network connection, wherein the detection controller is on the network side, and wherein the user physiological detection data is associated with an equipment ID of the corresponding medical detection equipment;
determining, by the detection controller on the network side, that the user ID information is associated with the user physiological detection data according to the associated and saved user ID information and equipment ID and according to the user physiological detection data associated with the equipment ID of the corresponding medical detection equipment; and
binding and sending, by the detection controller on the network side, the user physiological detection data and the associated user ID information from the detection controller to a data center.

2. The method according to claim 1, wherein before sending the detection start instruction from the detection controller to the corresponding medical detection equipment according to the equipment positioning information, the method further comprises:

verifying a validity of a user ID at least according to a matching result between user ID information saved on the network side and the received user ID information; and
sending the detection start instruction to the corresponding medical detection equipment according to the equipment positioning information when the verification is passed.

3. The method according to claim 1, wherein sending the detection start instruction from the detection controller to the corresponding medical detection equipment according to the equipment positioning information comprises:
sending, according to equipment location information comprised in the equipment ID, the detection start instruction from the detection controller to the medical detection equipment to which the equipment location information is directed or sending, according to associative information of the equipment ID and the equipment location information, the detection start instruction from the detection controller to the medical detection equipment to which the equipment location information associated with the equipment ID is directed when the equipment positioning information comprises the equipment ID; and
acquiring equipment ID or equipment location information of suitable medical detection equipment according to user location information and a selection policy and sending the detection start instruction from the detection controller to the corresponding medical detection equipment according to the equipment ID or the equipment location information when the equipment positioning information comprises the user location information.

4. The method according to claim 1, wherein the corresponding medical detection equipment does not have the user ID information.

5. The method according to claim 1, wherein the user ID information comprises a user's mobile phone number, an ID card number, a social security card number, or a medical card number.

6. The method according to claim 1, wherein the equipment ID comprises information obtained from a bar code, a two-dimensional image, or a radio frequency ID (RFID) chip.

7. The method according to claim 1, wherein the detection start instruction is configured to prompt the medical detection equipment to receive a user confirmation and send a confirming instruction or a detection start answer to the detection controller.

8. The method according to claim 1, further comprising keeping the user physiological detection data and the associated user ID information separate until the user physiological detection data and the associated user ID information are received by the detection controller, and combining the user physiological detection data and the associated user ID information at the detection controller before sending the user physiological detection data and the associated user ID information to the data center.

9. The method according to claim 8, further comprising receiving a detection complete instruction, confirming that a detection process is completed, and disassociating the user physiological detection data and the associated user ID information after the detection process is completed.

10. A telemedicine system, comprising:
medical detection equipment; and
a detection controller,
wherein the medical detection equipment is configured to receive and execute a control instruction sent by the detection controller, provide a user with a physiological index detection service, and send obtained user physiological detection data to the detection controller through a second channel, and wherein the detection controller is configured to:

receive detection related information comprising user identity (ID) information and equipment positioning information sent by handheld equipment through a first channel, wherein the second channel that sends the user physiological detection data and the first channel that receives the user ID information are different communication channels that each transfers data to the detection controller, wherein the first channel comprises a network channel that transfers the user ID information to the detection controller over a network connection, and wherein the detection controller is on a network side;

send a detection start instruction to corresponding medical detection equipment according to the equipment positioning information;

determine, by the detection controller on the network side, determine that the user ID information is associated with the user physiological detection data according to the associated and saved user ID information and equipment ID and according to the user physiological detection data associated with the equipment ID of the corresponding medical detection equipment; and bind and send the user physiological detection data and the associated user ID information to a data center after receiving the user physiological detection data that is associated with the equipment ID of the medical detection equipment and is sent by the medical detection equipment through the second channel.

11. The system according to claim 10, wherein the detection controller is further configured to verify a validity of the user ID and send the detection start instruction to the corresponding medical detection equipment according to the equipment positioning information after the verification of the user ID is passed.

12. The system according to claim 11, wherein the detection controller is specifically configured to output user location information to a location-based service engine after the verification of the user ID is passed, receive the equipment ID or equipment location information returned by the location-based service engine, and send the detection start instruction from the detection controller to the corresponding medical detection equipment according to the equipment ID or the equipment location information when the equipment positioning information comprises the user location information, and wherein the system further comprises the location-based service engine configured to determine suitable medical detection equipment according to the user location information and a selection policy and configured to return the equipment ID of the medical detection equipment or the equipment location information of the medical detection equipment to the detection controller.

13. The system according to claim 11, wherein the detection controller is specifically configured to output the equipment ID to a location-based service engine after the verification of the user ID is passed, receive the equipment location information returned by the location-based service engine, and send the detection start instruction to the corresponding medical detection equipment according to the equipment location information when the equipment positioning information comprises the equipment ID, wherein the system further comprises the location-based service engine configured to acquire the equipment location information of the corresponding medical detection equipment according to the equipment ID, and wherein the detection controller is specifically configured to send the detection start instruction to the medical detection equipment to which the equipment location information is directed according to the equipment location information comprised in the equipment ID or send the detection start instruction to the medical detection equipment to which the equipment location information associated with the equipment ID is directed according to associative information of the equipment ID and the equipment location information when the equipment positioning information comprises the equipment ID.

14. The system according to claim 10, further comprising the data center configured to associate the user physiological detection data sent by the detection controller with the user ID information and configured to save the associated user physiological detection data and user ID information.

15. The system according to claim 10, wherein the corresponding medical detection equipment does not have the user ID information.

16. The system according to claim 10, wherein the user ID information comprises a user's mobile phone number, an ID card number, a social security card number, or a medical card number, wherein the equipment ID comprises information obtained from a bar code, a two-dimensional image, or a radio frequency ID (RFID) chip, and wherein the detection start instruction is configured to prompt the medical detection equipment to receive a user confirmation and send a confirming instruction or a detection start answer to the detection controller.

17. A detection controller, comprising:

a receiver configured to receive detection related information sent by handheld equipment through a first channel and receive user physiological detection data sent by corresponding medical detection equipment through a second channel, wherein the detection related information comprises user identity (ID) information and equipment positioning information, wherein the first channel that receives the user ID information and the second channel that receives the user physiological detection data are different channels that each transmits data to the detection controller, wherein the first channel comprises a network channel that transfers the user ID information to the detection controller over a network connection, and wherein the detection controller is on a network side, and wherein the user physiological detection data is associated with an equipment ID of the corresponding medical detection equipment;

a processor configured to send a detection start instruction to the corresponding medical detection equipment according to the equipment positioning information; and a sender configured to determine that the user ID information is associated with the user physiological detection data according to the associated and saved user ID information and equipment ID and according to the user physiological detection data associated with the equipment ID of the corresponding medical detection equipment, and bind and send the user physiological detection data and the associated user ID information to a data center.

18. The detection controller according to claim 17, wherein the processor comprises a first processor configured to, after verification of the user ID is passed, send, according to equipment location information comprised in the equipment ID, the detection start instruction to the medical detection equipment to which the equipment location information is directed or send, according to associative information of the equipment ID and the equipment location information, the detection start instruction to the medical detection equipment to which the equipment location information associated with the equipment ID is directed when the equipment positioning information comprises the equipment ID of the medical detection equipment, wherein the processor comprises a second processor configured to, after the verification of the user ID is passed, output user location information to a location-based service engine, receive the equipment ID or equipment location information returned by the location-based service engine, and send the detection start instruction to the corresponding medical detection equipment according to the equipment ID or the equipment location information when the equipment positioning information comprises the user location information, and wherein the processor comprises a third processor configured to, after the verification of the user ID is passed, acquire equipment ID or equipment location information of suitable medical detection equipment according to the user location information and a selection policy, and send the detection start instruction to the corresponding medical detection equipment according to the equipment ID or the equipment location information when the equipment positioning information comprises the user location information.

19. The detection controller according to claim 17, wherein the corresponding medical detection equipment does not have the user ID information.

20. The detection controller according to claim 17, wherein the user ID information comprises a user's mobile phone number, an ID card number, a social security card number, or a medical card number, wherein the equipment ID comprises information obtained from a bar code, a two-dimensional image, or a radio frequency ID (RFID) chip, and wherein the detection start instruction is configured to prompt the medical detection equipment to receive a user confirmation and send a confirming instruction or a detection start answer to the detection controller.

\* \* \* \* \*

UNITED STATES PATENT AND TRADEMARK OFFICE
CERTIFICATE OF CORRECTION

PATENT NO. : 8,868,681 B2  
APPLICATION NO. : 13/306474  
DATED : October 21, 2014  
INVENTOR(S) : Zhongqing Xu et al.

Page 1 of 1

It is certified that error appears in the above-identified patent and that said Letters Patent is hereby corrected as shown below:

In the Claims

Col. 18 line 62 - Col. 19 line 3, Claim 10 should read:

A telemedicine system, comprising:
medical detection equipment; and
a detection controller,
wherein the medical detection equipment is configured to receive and execute a control instruction sent by the detection controller, provide a user with a physiological index detection service, and send obtained user physiological detection data to the detection controller through a second channel, and wherein the detection controller is configured to:
receive detection related information comprising user identity (ID) information and equipment positioning information sent by handheld equipment through a first channel, wherein the second channel that sends the user physiological detection data and the first channel that receives the user ID information are different communication channels that each transfers data to the detection controller, wherein the first channel comprises a network channel that transfers the user ID information to the detection controller over a network connection, and wherein the detection controller is on a network side;
send a detection start instruction to corresponding medical detection equipment according to the equipment positioning information;
determine, by the detection controller on the network side, that the user ID information is associated with the user physiological detection data according to the associated and saved user ID information and equipment ID and according to the user physiological detection data associated with the equipment ID of the corresponding medical detection equipment; and
bind and send the user physiological detection data and the associated user ID information to a data center after receiving the user physiological detection data that is associated with the equipment ID of the medical detection equipment and is sent by the medical detection equipment through the second channel.

Signed and Sealed this
Third Day of February, 2015

Michelle K. Lee
*Deputy Director of the United States Patent and Trademark Office*